(12) United States Patent
Okamura et al.

(10) Patent No.: US 7,377,691 B2
(45) Date of Patent: *May 27, 2008

(54) RADIOGRAPHIC APPARATUS THAT REMOVES TIME LAG BY RECURSIVE COMPUTATION

(75) Inventors: Shoichi Okamura, Nara-ken (JP); Keiichi Fujii, Kyoto-fu (JP); Susumu Adachi, Osaka-fu (JP); Shinya Hirasawa, Kyoto-fu (JP); Toshinori Yoshimuta, Osaka-fu (JP); Koichi Tanabe, Kyoto-fu (JP); Masatomo Kaino, Osaka-fu (JP); Hiroshi Koyama, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 68 days.

This patent is subject to a terminal disclaimer.

(21) Appl. No.: 10/758,022

(22) Filed: Jan. 16, 2004

(65) Prior Publication Data

US 2004/0156481 A1    Aug. 12, 2004

(30) Foreign Application Priority Data

Feb. 12, 2003    (JP) .............................. 2003-033389

(51) Int. Cl.
*H05G 1/64*    (2006.01)
*G01D 18/00*    (2006.01)

(52) U.S. Cl. ....................... 378/207; 378/19; 378/98.8; 250/370.09

(58) Field of Classification Search .................. 378/4, 378/19, 42, 62, 91, 98.8, 190, 207; 250/370.09
See application file for complete search history.

(56) References Cited

U.S. PATENT DOCUMENTS

| | | | | |
|---|---|---|---|---|
| 5,249,123 | A | | 9/1993 | Hsieh |
| 5,265,013 | A | * | 11/1993 | King et al. .................... 378/4 |
| 5,359,638 | A | * | 10/1994 | Hsieh et al. ................... 378/4 |
| 5,517,544 | A | * | 5/1996 | Levinson ....................... 378/4 |
| 5,644,610 | A | * | 7/1997 | Crawford et al. ............. 378/19 |
| 6,041,097 | A | * | 3/2000 | Roos et al. ................... 378/62 |
| 6,493,646 | B1 | * | 12/2002 | Hsieh et al. ................. 702/104 |
| 6,949,746 | B2 | * | 9/2005 | Stierstorfer .............. 250/336.1 |
| 7,003,071 | B2 | * | 2/2006 | Nagaoka et al. ............. 378/19 |
| 2005/0036582 | A1 | * | 2/2005 | Nagaoka et al. ............. 378/19 |

* cited by examiner

*Primary Examiner*—Allen C. Ho
(74) *Attorney, Agent, or Firm*—Cheng Law Group PLLC

(57) ABSTRACT

A radiographic apparatus obtains lag-free radiation detection signals with lag-behind parts removed from radiation detection signals taken from a flat panel X-ray detector as X rays are emitted from an X-ray tube. The lag-behind parts are removed by a recursive computation on an assumption that the lag-behind part included in each X-ray detection signal is due to an impulse response formed of exponential functions, N in number, with different attenuation time constants. X-ray images are created from the lag-free radiation detection signals.

4 Claims, 6 Drawing Sheets

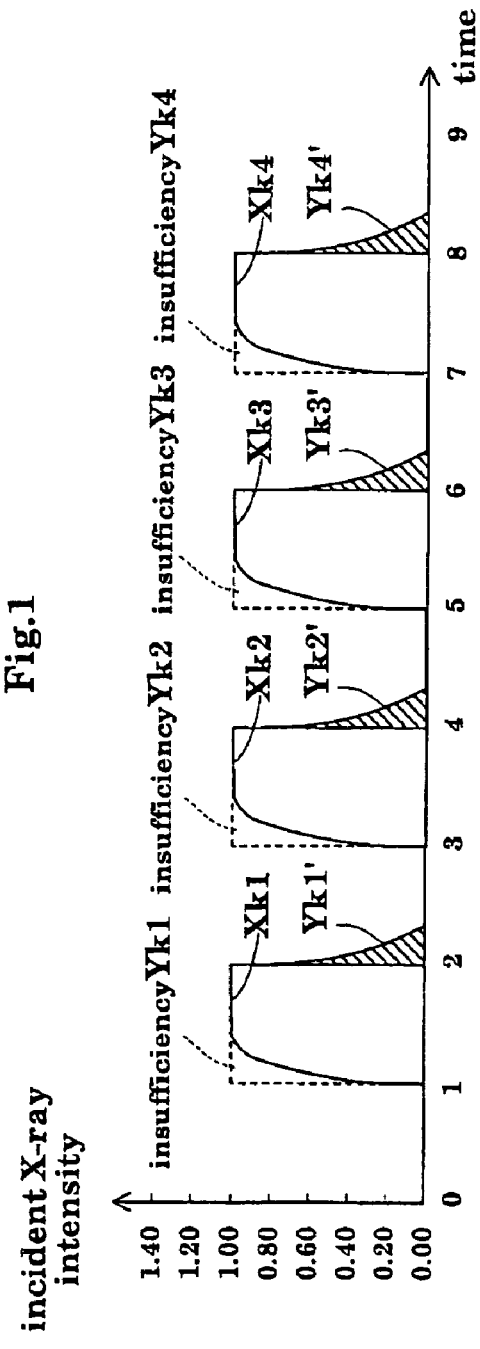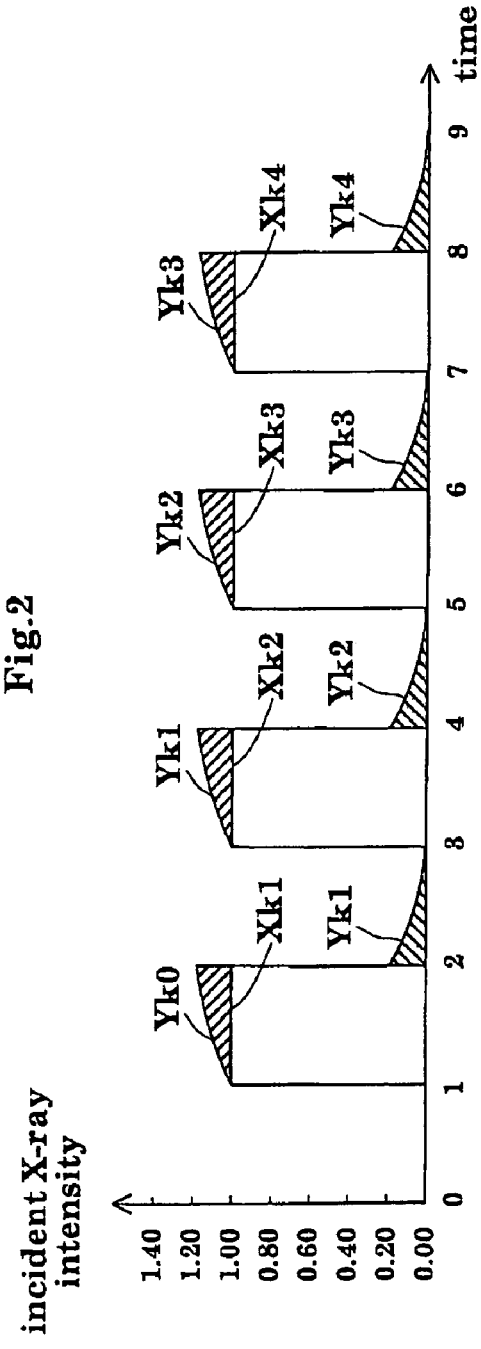

RADIOGRAPHIC APPARATUS THAT REMOVES TIME LAG BY RECURSIVE COMPUTATION

BACKGROUND OF THE INVENTION (1) Field of the Invention

This invention relates to a radiographic apparatus for medical or industrial use, for obtaining radiographic images based on radiation detection signals fetched at predetermined sampling time intervals by a signal sampling device from a radiation detecting device as radiation is emitted from a radiation emitting device. More particularly, the invention relates to a technique for fully eliminating time lags, due to the radiation detecting device, of the radiation detection signals taken from the radiation detecting device.

(2) Description of the Related Art

In a medical fluoroscopic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, the fluoroscopic apparatus is constructed to obtain an X-ray image corresponding to an X-ray penetration image of a patient for every period between sampling intervals, based on X-ray detection signals for one X-ray image taken at sampling time intervals from the FPD as the patient is irradiated with X rays from the X-ray tube. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive radiation detection signal $x_k$ with a lag-behind part removed from radiation detection signal $y_k$:

$$x_k = [y_k - \Sigma_{n=1}^{N}\{\alpha_n \cdot [1-\exp(T_n)] \cdot \exp(T_n) \cdot S_{nk}\}]$$

$$/\Sigma_{n=1}^{N} \beta_n$$

in which $T_n = \Delta t/\tau_n$, $S_{nk} = x_{k-1} + \exp(T_n) \cdot S_{n(k-1)}$, and $\beta_n = \alpha_n \cdot [1-\exp(T_n)]$, where $\Delta t$: sampling intervals;

k: subscript representing a k-th point of time in a sampling time series;

N: the number of exponential functions with different time constants forming the impulse response;

n: subscript representing one of the exponential functions forming the impulse response;

$\alpha_n$: intensity of exponential function n; and $\tau_n$: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. That is, it has been confirmed that the time lag of the FPD is not eliminated (see U.S. Pat. No. 5,249,123).

Further, U.S. Pat. No. 5,517,544 discloses a different proposal to solve the problem of the time lag caused by the FPD in acquiring CT images. This technique assumes a time lag of the FPD to be approximated by one exponential function, and removes a lag-behind part from a radiation detection signal by computation. Inventors herein have carefully reviewed the computation technique proposed in this U.S. patent. It has been found, however, that it is impossible for one exponential function to approximate the time lag of the FPD, and the time lag of the FPD is not eliminated by this technique, either (see U.S. Pat. No. 5,517,544).

SUMMARY OF THE INVENTION

This invention has been made having regard to the state of the art noted above, and its object is to provide a radiographic apparatus for fully eliminating time lags, due to a radiation detecting device, of radiation detection signals taken from the radiation detecting device.

The above object is fulfilled, according to this invention, by a radiographic apparatus for obtaining radiographic images, comprising:

a radiation emitting device for emitting radiation toward an object under examination;

a signal sampling device for taking radiation detection signals from a radiation detecting device at predetermined sampling time intervals; and a time lag removing device for obtaining lag-free radiation detection signals by removing the lag-free radiation detection signals from the respective radiation detection signals by a recursive computation, on an assumption that a lag-behind part included in each of the radiation detection signals taken by the signal sampling device at the predetermined sampling time intervals is due to an impulse response formed of one exponential function or a plurality of exponential functions with different attenuation time constants;

the radiographic images being derived from the lag-free radiation detection signals obtained by the time lag removing device.

According to this invention, radiation detection signals are outputted from the radiation detecting device at predetermined sampling time intervals as radiation is emitted from the radiation emitting device to an object under examination. The time lag removing device carries out a recursive computation, on-time (in real time) or off-time (in non-real time), on an assumption that a lag-behind part included in each of the radiation detection signals is due to an impulse response formed of one exponential function or a plurality of exponential functions with different attenuation time constants. That is, a lag-free radiation detection signal is obtained by removing a lag-behind part from each radiation detection signal. From such lag-free radiation detection signals with the lag-behind parts fully removed, clear radiographic images may be obtained without a double image and blurring due to an after effect of a preceding image.

In particular, the lag-free radiation detection signals are obtained with the lag-behind parts more completed removed when the recursive computation is carried out on the assumption that a lag-behind part included in each radiation detection signal is due to an impulse response formed of a plurality of exponential functions with different attenuation time constants, than when the recursive computation is carried out on the assumption that a lag-behind part included in each radiation detection signal is due to an impulse response formed of one exponential function.

In this invention, the time lag removing device, preferably, is arranged to perform the recursive computation for removing the lag-behind part from each of the radiation detection signals, based on the following equations A-C:

$$X_k = Y_k - \Sigma_{n=1}^{N} \{\alpha_n \cdot [1 - \exp(T_n)] \cdot \exp(T_n) \cdot S_{nk}\} \quad \text{A}$$

$$T_n = -\Delta t / \tau_n \quad \text{B}$$

$$S_{nk} = X_{k-1} + \exp(T_n) \cdot S_{n(k-1)} \quad \text{C}$$

where $\Delta t$: the sampling time interval;

k: a subscript representing a k-th point of time in a sampling time series;

$Y_k$: an X-ray detection signal taken at the k-th sampling time;

$X_k$: a lag-free X-ray detection signal with a lag-behind part removed from the signal $Y_k$;

$X_{k-1}$: a signal $X_k$ taken at a preceding point of time;

$S_{n(k-1)}$: an $S_n$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

With this construction, the lag-free X-ray detection signal $X_k$ may be derived promptly from equations A-C constituting a compact recurrence formula. That is, when, as shown in FIG. 8, a fixed quantity of radiation impinges on the radiation detecting device during a period t0-t1, the radiation detection signal will have a fixed value as indicated in an alternate long and short dash line in FIG. 9 if the radiation detecting device causes no time lag.

In practice, however, a time lag is caused by the radiation detecting device to add a lag-behind part as shown in oblique hatches in FIG. 9. This results in the radiation detection signal $Y_k$ shown in a solid line in FIG. 9. In this invention, the second term in equation A "$\Sigma_{n=1}^{N} \{\alpha_n \cdot [1 - \exp(T_n)] \cdot \exp(T_n) \cdot S_{nk}\}$" corresponds to the lag-behind part shown in the oblique hatches in FIG. 9. This lag-behind part is taken away from the radiation detection signal $Y_k$. Consequently, the lag-free radiation detection signal $X_k$ no longer has the lag-behind part shown in the alternate long and short dash line in FIG. 9.

A review made by Inventors herein shows that the equation proposed in U.S. Pat. No. 5,249,123 merely provides a lag-behind part of a radiation detection signal shown in a solid line in FIG. 1. It has been confirmed that this U.S. patent cannot obtain the radiation detection signal without the lag-behind part shown in the alternate long and short dash line in FIG. 9.

It is preferred, according to this invention, that the signal sampling device is arranged to start taking the radiation detection signals at the sampling time intervals before emission of the radiation, and the time lag removing device is arranged to obtain the lag-free radiation detection signals by using the radiation detection signals taken before emission of the radiation.

With this construction, the time lag removing device can obtain lag-free radiation detection signals by using the radiation detection signals taken by the signal sampling device before emission of the radiation. Consequently, lag-free X-ray detection signals may properly be obtained immediately upon emission of the radiation by removing the lag-behind parts included in the radiation detection signals.

Preferably, the signal sampling device is arranged to take the radiation detection signals for one radiographic image continually at each period between the sampling time intervals, and the time lag removing device is arranged to obtain, continually at each period between the sampling time intervals, the lag-free radiation detection signals corresponding to the radiation detection signals for the one radiographic image, the radiographic images being obtained continually at the sampling time intervals from the lag-free radiation detection signals for dynamic display.

With this construction, each radiographic image is free from a time lag, which enables a clear dynamic display without blurring by an after-effect of a preceding image.

It is still more desirable that a computation of the lag-free radiation detection signals and an acquisition and dynamic image display of the radiographic images are performed in real time.

This construction allows a dynamic display of radiographic images to be made in real time.

According to this invention, the radiation detecting device may be a flat panel X-ray detector having numerous radiation detecting elements formed of a semiconductor and arranged longitudinally and transversely on a radiation detecting surface.

Where a flat panel X-ray detector is used, the time lag removing device eliminates the time lags of the radiation detecting signals caused by the flat panel X-ray detector. It is also possible to remove complicated detecting distortions from output images.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 1 is a view showing a result of a time lag removal from a radiation detection signal by a conventional technique;

FIG. 2 is a block diagram showing an overall construction of a fluoroscopic apparatus in a first embodiment of the invention;

DESCRIPTION OF THE PREFERRED EMBODIMENTS

Figure 3:
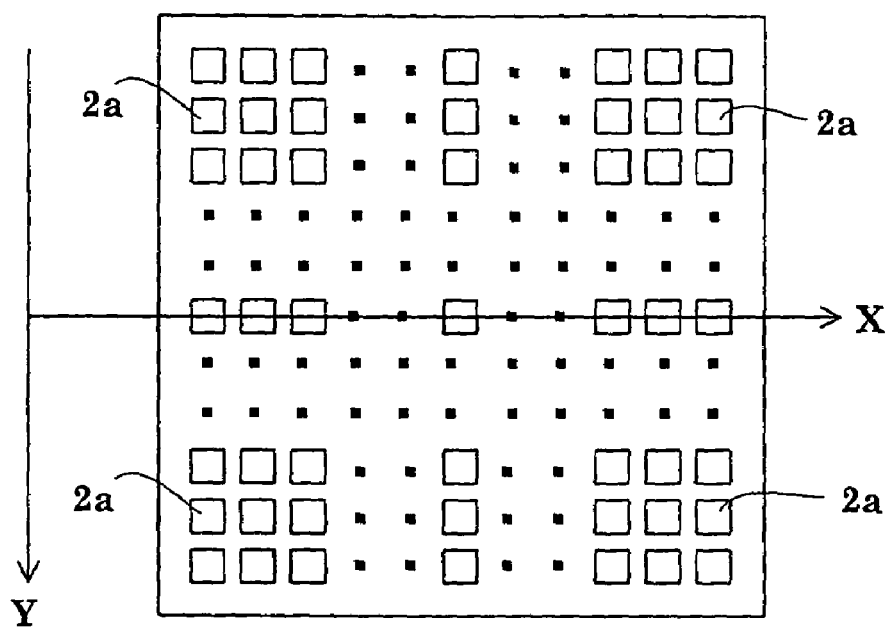
FIG. 3 is a plane view of an FPD used in the first embodiment.

Preferred embodiments of this invention will be described in detail hereinafter with reference to the drawings.

First Embodiment

FIG. 2 is a block diagram showing an overall construction of a fluoroscopic apparatus in a first embodiment.

As shown in FIG. 2, the fluoroscopic apparatus includes an X-ray tube (radiation emitting device) 1 for emitting X rays toward a patient M, an FPD (radiation detecting device) 2 for detecting X rays transmitted through the patient M, an analog-to-digital converter (signal sampling device) 3 for digitizing X-ray detection signals (radiation detection signals) taken from the FPD (flat panel X-ray detector) 2 at predetermined sampling time intervals Δt, a detection signal processor 4 for creating X-ray images based on X-ray detection signals outputted from the analog-to-digital converter 3, and an image monitor 5 for displaying the X-ray images created by the detection signal processor 4. That is, the apparatus is constructed to acquire X-ray images from the X-ray detection signals taken from the FPD 2 by the analog-to-digital converter 3 as the patient M is irradiated with X rays, and display the acquired X-ray images on the screen of the image monitor 5. Each component of the apparatus in the first embodiment will particularly be described hereinafter.

The X-ray tube 1 and FPD 2 are opposed to each other across the patient M. In time of X-ray radiography, the X-ray tube 1 is controlled by an X-ray emission controller 6 to emit X rays in the form of a cone beam to the patient M. At the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 7 and an X-ray detector moving mechanism 8, respectively. In moving the X-ray tube 1 and FPD 2, the X-ray tube moving mechanism 7 and X-ray detector moving mechanism 8 are controlled by an irradiating and detecting system movement controller 9 to move the X-ray tube 1 and FPD 2 together as opposed to each other, with the center of emission of X rays constantly in agreement with the center of the X-ray detecting surface of FPD 2. Of course, movement of the X-ray tube 1 and FPD 2 results in variations in the position of the patient M irradiated with X rays, hence movement of a radiographed site.

As shown in FIG. 3, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1024 by 1024 on the X-ray detecting surface about 30 cm long and 30 cm wide. Each X-ray detecting element 2a of FPD 2 corresponds to one pixel in an X-ray image created by the detection signal processor 4. Based on the X-ray detection signals taken from the FPD 2, the detection signal processor 4 creates an X-ray image corresponding to a penetration X-ray image projected to the X-ray detecting surface.

The analog-to-digital converter 3 continually takes X-ray detection signals for each X-ray image at sampling time intervals Δt, and stores the X-ray detection signals for X-ray image creation in a memory 10 disposed downstream of the converter 3. An operation for sampling (extracting) the X-ray detection signals is started before X-ray irradiation (in an offset state).

Figure 4:
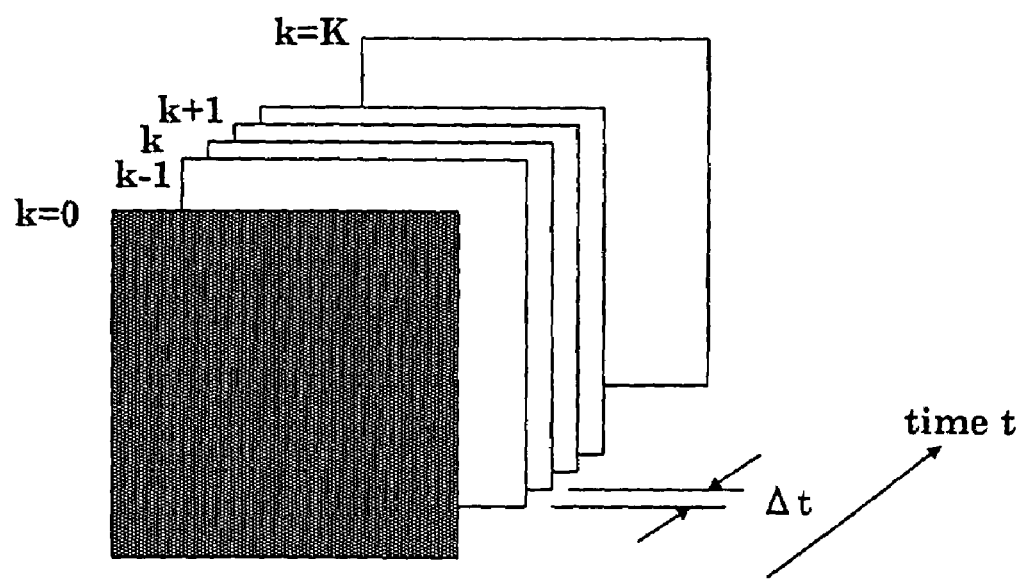
FIG. 4 is a schematic view showing a state of sampling X-ray detection signals during X-ray radiography in the first embodiment.

That is, as shown in FIG. 4, all X-ray detection signals for a penetration X-ray image are collected at each period between the sampling intervals Δt, and are successively stored in the memory 10. The sampling of X-ray detection signals by the analog-to-digital converter 3 may be started before an emission of X rays manually by the operator or automatically as interlocked with a command for X-ray emission.

As shown in FIG. 2, the fluoroscopic apparatus in the first embodiment includes a time lag remover 11 for obtaining lag-free radiation detection signals. A lag-free radiation detection signal is removed from each radiation detection signal by a recursive computation based on an assumption that a lag-behind part included in each of the X-ray detection signals taken at the sampling time intervals from the FPD 2 is due to an impulse response formed of a plurality of exponential functions with different attenuation time constants.

Figure 9:
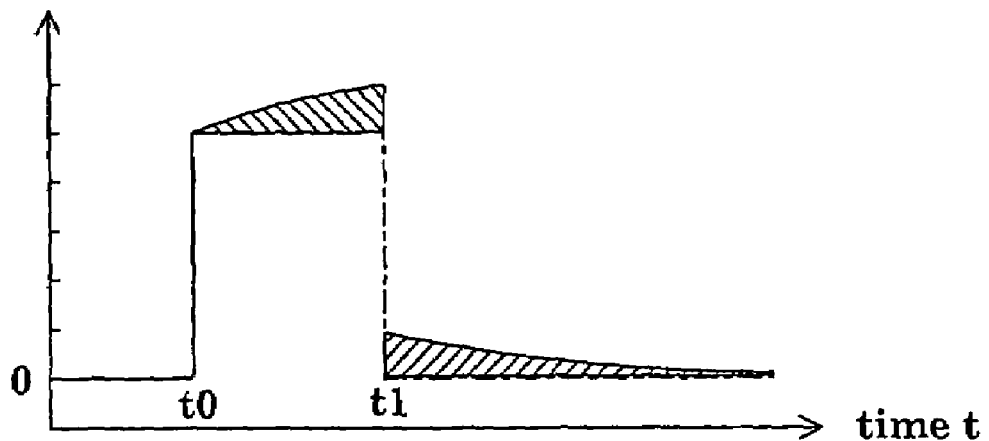
FIG. 9 is a view showing a time lag of a radiation detection signal.

The FPD 2 has part of an X-ray detection signal left unfetched as shown in a solid line in FIG. 9, and this part remains as a lag-behind part (hatched part) after the signal is taken away. The time lag remover 11 removes this lag-behind part to produce a lag-free X-ray detection signal. Based on such lag-free X-ray detection signals, the detection signal processor 4 creates an X-ray image corresponding to a penetration X-ray image to be projected to the X-ray detecting surface.

Specifically, the time lag remover 11 performs a recursive computation processing for removing a lag-behind part from each X-ray detection signal by using the following equations A-C:

$$X_k = Y_k - \Sigma_{n=1}^{N}\{\alpha_n \cdot [1-\exp(T_n)] \cdot \exp(T_n) \cdot S_{nk}\} \quad\quad A$$

$$T_n = -\Delta t / \tau_n \quad\quad B$$

$$S_{nk} = X_{k-1} + \exp(T_n) \cdot S_{n(k-1)} \quad\quad C$$

where Δt is the sampling time interval; k is a sub-script representing a k-th point of time in a sampling time series; $Y_k$ is an X-ray detection signal taken at the k-th sampling time; $X_k$ is a lag-free X-ray detection signal with a lag-behind part removed from the signal $Y_k$; $X_{k-1}$ is a signal $X_k$ taken at a preceding point of time; $S_{n(k-1)}$ is an $S_n$ at a preceding point of time; exp is an exponential function; N is the number of exponential functions with different time constants forming the impulse response; n is a subscript representing one of the exponential functions forming the impulse response; $\alpha_n$ is an intensity of exponential function n; and $\tau_n$ is an attenuation time constant of exponential function n.

That is, the second term in equation A "$\Sigma_{n=1}^{N}\{\alpha_n \cdot [1-\exp(T_n)] \cdot \exp(T_n) \cdot S_{nk}\}$" corresponds to the lag-behind part. Thus, the apparatus in the first embodiment derives the lag-free X-ray detection signal $X_k$ promptly from equations A-C constituting a compact recurrence formula.

In the first embodiment, the analog-to-digital converter 3, detection signal processor 4, X-ray emission controller 6, irradiating and detecting system movement controller 9 and time lag remover 11 are operable on instructions and data inputted from an operating unit 12 or on various commands outputted from a main controller 13 with progress of X-ray radiography.

Next, an operation for performing X-ray radiography with the apparatus in the first embodiment will particularly be described with reference to the drawings.

Figure 5:
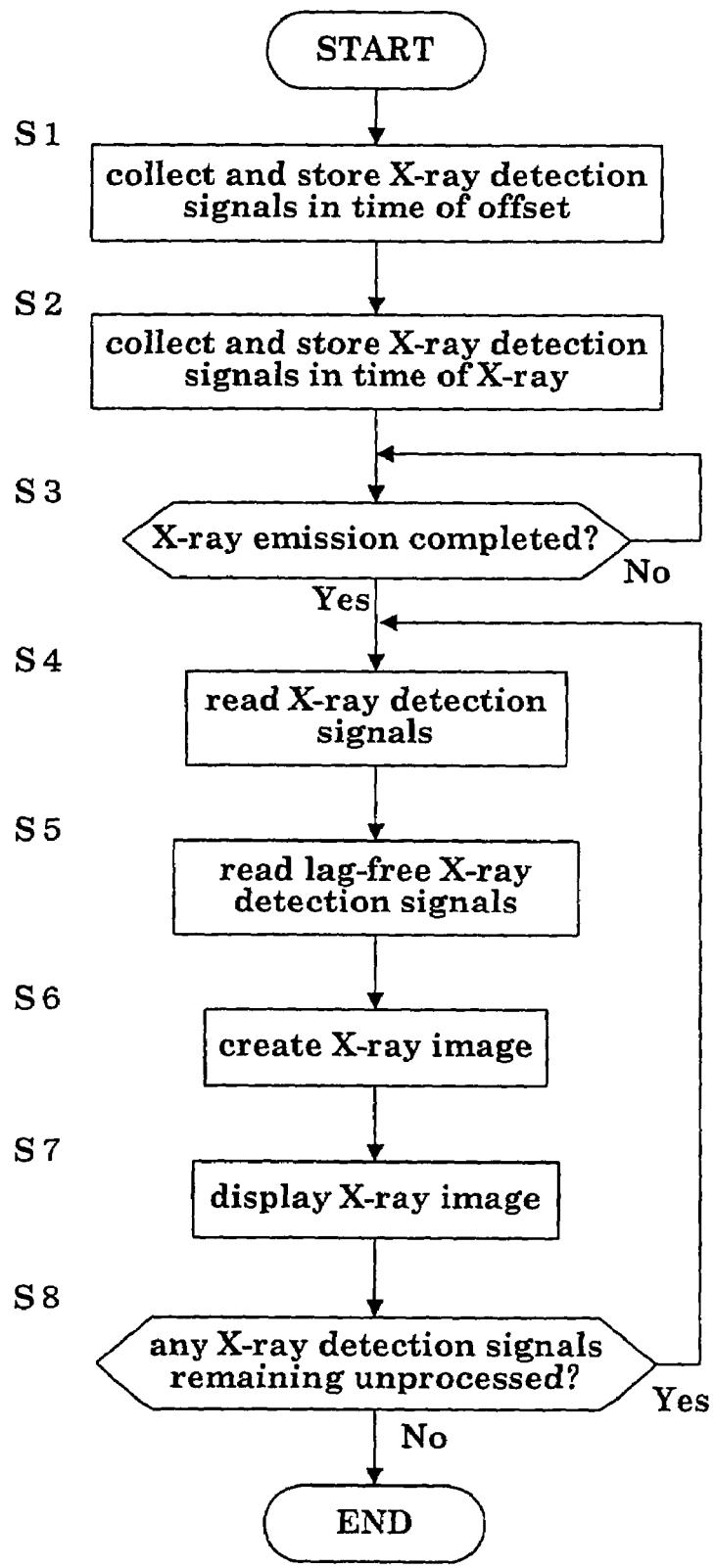
FIG. 5 is a flow chart showing a procedure of X-ray radiography in the first embodiment.

FIG. 5 is a flow chart showing a procedure of X-ray radiography in the first embodiment.

[Step S1] The analog-to-digital converter 3 starts taking X-ray detection signals $Y_k$ for one X-ray image from the FPD 2 at each period between the sampling time intervals Δt (=1/30 second) before X-ray emission (in an offset state). The X-ray detection signals taken are stored in the memory 10.

[Step S2] In parallel with a continuous or intermittent X-ray emission to the patient M initiated by the operator, the analog-to-digital converter 3 continues taking X-ray detection signals $Y_k$ for one X-ray image at each period between the sampling time intervals Δt and storing the signals in the memory 10.

[Step S3] When the X-ray emission is completed, the operation proceeds to step S4. When the X-ray emission is uncompleted, the operation returns to step S2.

[Step S4] X-ray detection signals $Y_k$ for one X-ray image collected in one sampling sequence are read from the memory 10.

[Step S5] The time lag remover 11 performs the recursive computation based on the equations A-C, and derives lag-free X-ray detection signals $X_k$, i.e. pixel values, with lag-behind parts removed from the respective X-ray detection signals $Y_k$.

[Step S6] The detection signal processor 4 creates an X-ray image based on the lag-free X-ray detection signals $X_k$ for one sampling sequence (for one X-ray image).

[Step S7] The X-ray image created is displayed on the image monitor 5.

[Step S8] When unprocessed X-ray detection signals $Y_k$ remain in the memory 10, the operation returns to step S4. When no unprocessed X-ray detection signals $Y_k$ remain, the X-ray radiography is ended.

In the first embodiment, the time lag remover 11 computes the lag-free X-ray detection signals $X_k$ corresponding to the X-ray detection signals $Y_k$ for one X-ray image, and the detection signal processor 4 creates an X-ray image, both at each period between the sampling time intervals Δt (=1/30 second). That is, the apparatus is constructed also for creating X-ray images one after another at a rate of about 30 images per second, and displaying the created X-ray images continuously. It is thus possible to perform a dynamic display of X-ray images.

Since each X-ray image has lag-behind parts removed therefrom, the apparatus in this embodiment is capable of a clear dynamic image display free from double images due to an aftereffect of preceding images even when a radiographed site moves during a radiographic operation.

Figure 6:
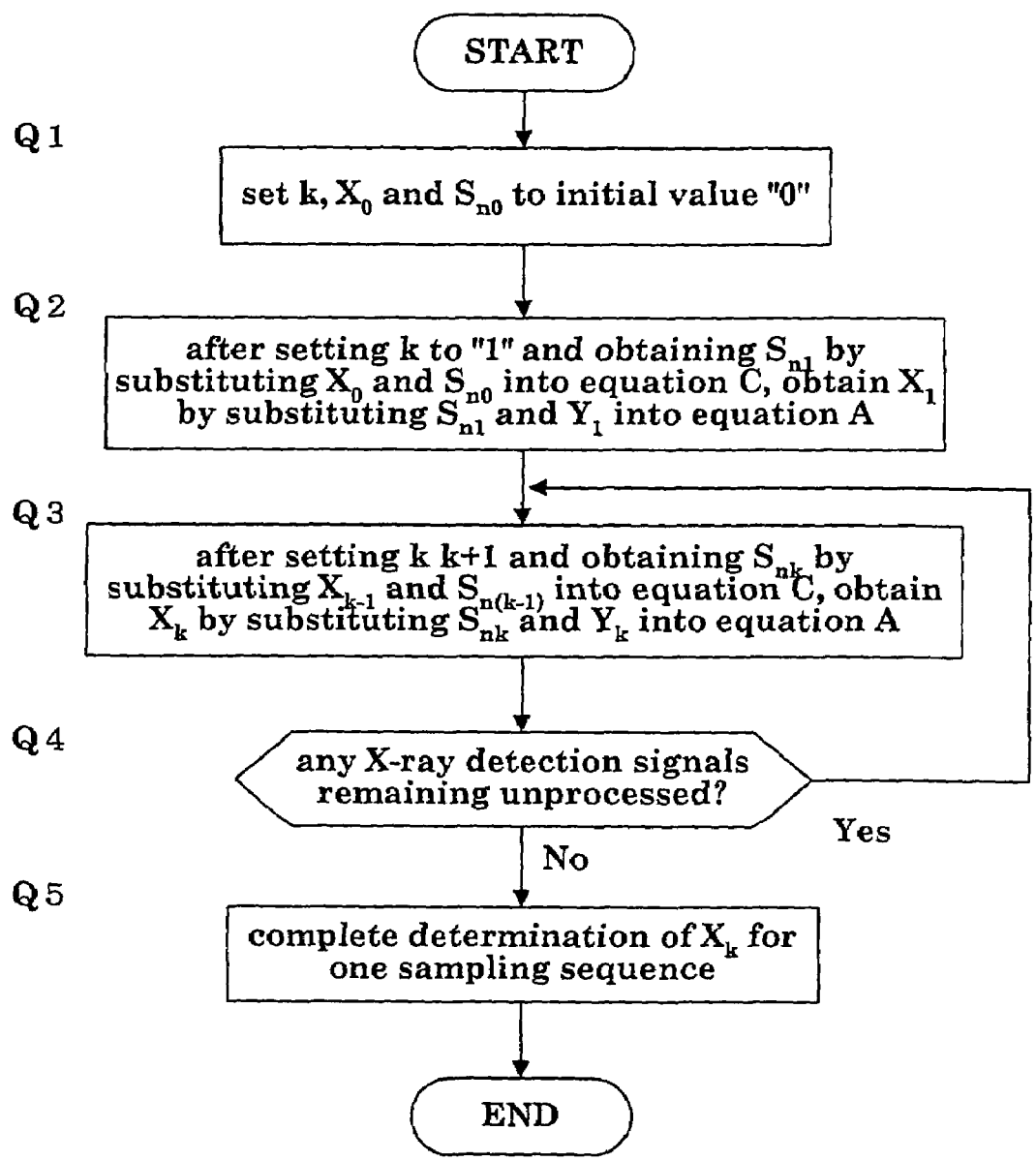
FIG. 6 is a flow chart showing a recursive computation process for time lag removal in the first embodiment.

Next, the process of recursive computation carried out in the above step S5 by the time lag remover 11 will particularly be described. FIG. 6 is a flow chart showing a recursive computation process for time lag removal in the first embodiment

[Step Q1] A setting k=0 is made, and $X_0$=0 in equation A and $S_{n0}$=0 in equation C are set as initial values before X-ray emission. Where the number of exponential functions is three (N=3), $S_{10}$, $S_{20}$ and $S_{30}$ are all set to 0.

[Step Q2] In equations A and C, k=1 is set. $S_{11}$, $S_{21}$ and $S_{31}$ are derived from equation C, i.e. $S_{n1}=X_0+\exp(T_n)S_{n0}$. Further, lag-free X-ray detection signal $X_1$ is obtained by substituting $S_{11}$, $S_{21}$ and $S_{31}$ derived and X-ray detection signal $Y_1$ into equation A.

[Step Q3] After incrementing k by 1 (k=k+1) in equations A and C, S1 k, S2 k and S3 k are obtained by substituting $X_{k-1}$ of a preceding time into equation C. Further, lag-free X-ray detection signal $X_k$ is obtained by substituting $S_{1k}$, $S_{2k}$ and $S_{3k}$ derived and X-ray detection signal $Y_k$ into equation A.

[Step Q4] When there remain unprocessed X-ray detection signals $Y_k$, the operation returns to step Q3. When no unprocessed X-ray detection signals $Y_k$ remain, the operation proceeds to step Q5.

[Step Q5] Lag-free X-ray detection signals $X_k$ for one sampling sequence (for one X-ray image) are obtained to complete the recursive computation for the one sampling sequence.

According to the fluoroscopic apparatus in the first embodiment, as described above, when the time lag remover 11 obtains a lag-free X-ray detection signal by removing a lag-behind part from each X-ray detection signal by the recursive computation, an assumption is made that the lag-behind part included in each X-ray detection signal is due to an impulse response formed of a plurality of exponential functions with different attenuation time constants. Thus, the lag-free X-ray detection signal obtained has the lag-behind part fully removed, compared with the case of assuming that the lag-behind part is due to an impulse response formed of a single exponential function.

In the first embodiment, the time lag remover 11 may obtain lag-free X-ray detection signals by using X-ray detection signals taken by the analog-to-digital converter 3 before X-ray emission (in an offset state). Consequently, in time of the X-ray emission, lag-free X-ray detection signals may properly be obtained immediately upon X-ray emission by removing lag-behind parts included in the X-ray detection signals.

Second Embodiment

In the second embodiment, the time lag remover 11 computes the lag-free X-ray detection signals $X_k$ corresponding to the X-ray detection signals $Y_k$ for one X-ray image, and the detection signal processor 4 creates X-ray images, both at each period between the sampling time intervals Δt (=1/30 second).

This embodiment has the same construction and function as the first embodiment except that the apparatus is constructed for creating X-ray images one after another in real time at a rate of about 30 images per second, and displaying the created X-ray images continuously in real time. The features common to the first embodiment will not be described, and description will be made on what is different from the first embodiment.

An operation for performing X-ray radiography with the apparatus in the second embodiment will be described with reference to the drawings.

Figure 7:
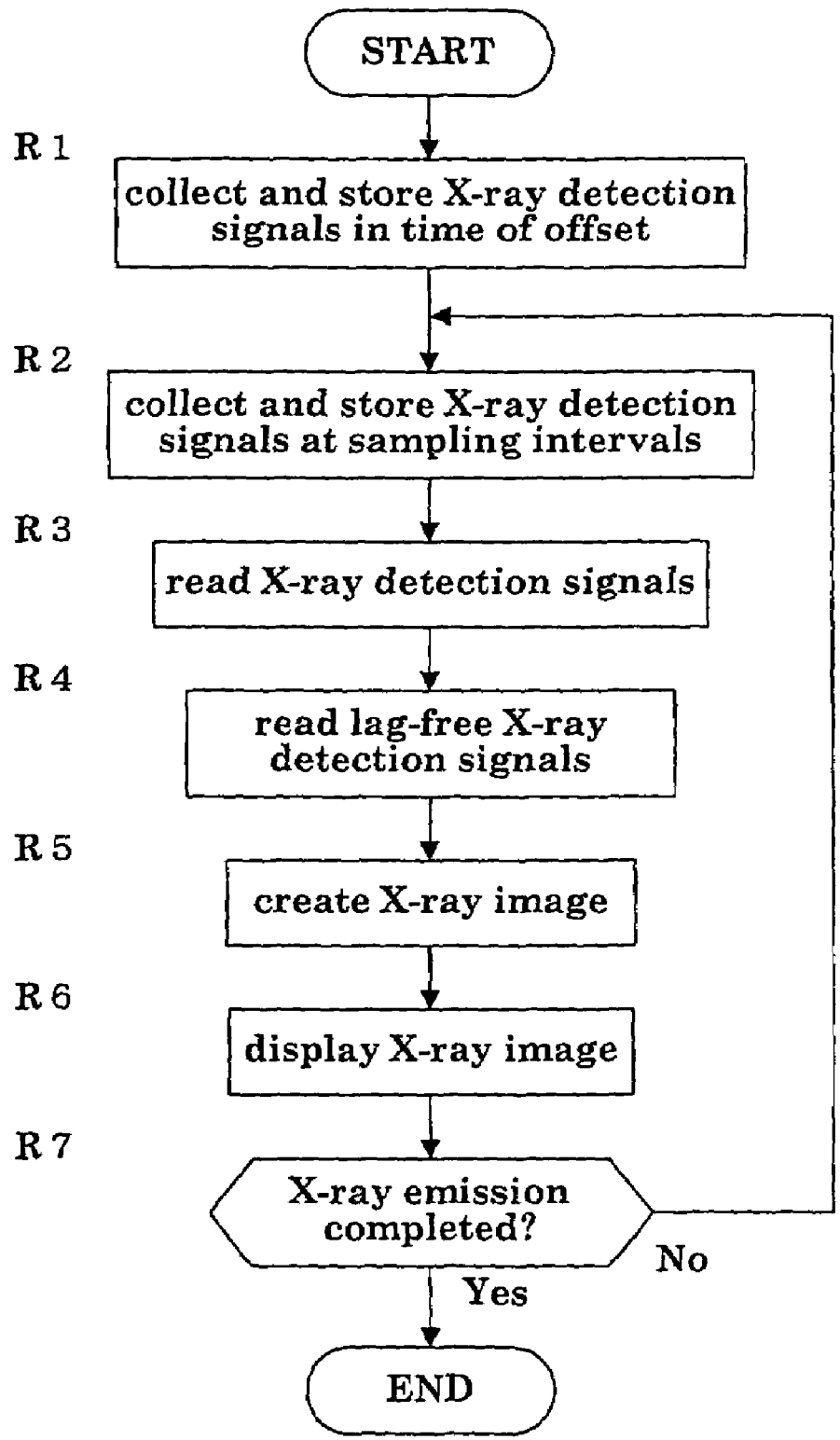
FIG. 7 is a flow chart showing a procedure of X-ray radiography in a second embodiment.
Figure 8:
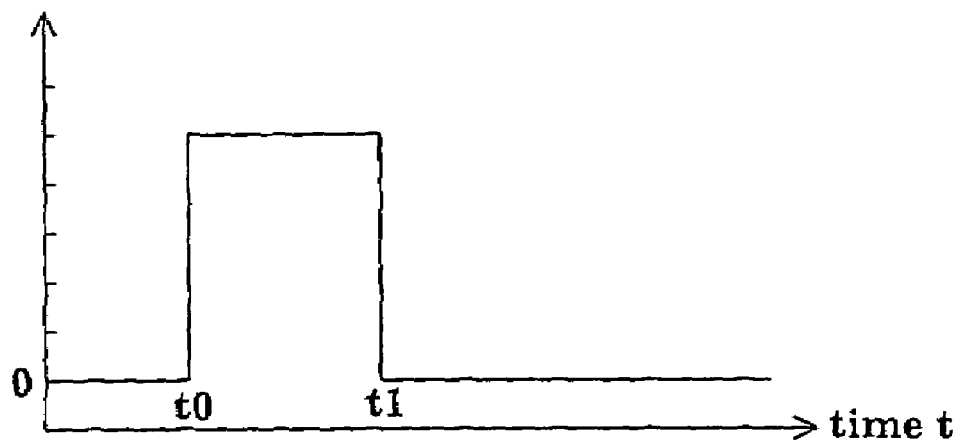
FIG. 8 is a view showing a state of radiation incidence on an X-ray detecting device.

FIG. 7 is a flow chart showing a procedure of X-ray radiography in the second embodiment.

[Step R1] The analog-to-digital converter 3 starts taking X-ray detection signals $Y_k$ for one X-ray image from the FPD 2 at each period between the sampling time intervals Δt (=1/30 second) before X-ray emission (in an offset state). The X-ray detection signals taken are stored in the memory 10.

[Step R2] In parallel with a continuous or intermittent X-ray emission to the patient M initiated by the operator, the analog-to-digital converter 3 continues taking X-ray detection signals $Y_k$ for one X-ray image at each period between the sampling time intervals Δt and storing the signals in the memory 10.

[Step R3] X-ray detection signals $Y_k$ for one X-ray image collected in one sampling sequence are read from the memory 10.

[Step R4] The time lag remover 11 performs the recursive computation based on the equations A-C, and derives lag-free X-ray detection signals $X_k$, i.e. pixel values, with lag-behind parts removed from the respective X-ray detection signals $Y_k$.

[Step R5] The detection signal processor 4 creates an X-ray image based on the lag-free X-ray detection signals $X_k$ for one sampling sequence (for one X-ray image).

[Step R6] The X-ray image created is immediately displayed on the image monitor 5.

[Step R7] When the X-ray emission is uncompleted, the operation returns to step R2. When the X-ray emission is completed, the X-ray radiography is terminated.

According to the second embodiment, as described above, X-ray images are created and displayed in real time at the sampling time intervals Δt (=1/30 second), i.e. at the rate of about 30 images per second. It is thus possible to perform a dynamic display of X-ray images in real time.

This invention is not limited to the foregoing embodiments, but may be modified as follows:

(1) The first and second embodiments described above employ an FPD as the radiation detecting device. This invention is applicable also to an apparatus having a radiation detecting device other than an FPD that causes time lags of X-ray detection signals.

(2) The apparatus in the first embodiment described above may be constructed to allow a selection for causing the time lag remover 11 to compute lag-free X-ray detection signals $X_k$, and for the detection signal processor 4 to create X-ray images, both in real time, as in the second embodiment.

(3) While the apparatus in the first and second embodiments are fluoroscopic apparatus, this invention is applicable also to an apparatus other than the fluoroscopic apparatus, such as an X-ray CT apparatus.

(4) The apparatus in the first and second embodiments are designed for medical use. This invention is applicable not only to such medical apparatus but also to an apparatus for industrial use such as a nondestructive inspecting apparatus.

(5) The apparatus in the first and second embodiments use X rays as radiation. This invention is applicable also to an apparatus using radiation other than X rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining radiographic images, comprising:

radiation emitting means for emitting radiation toward an object under examination;

a flat panel X-ray detector as a radiation detection means for detecting the radiation emitted toward the object under examination from said radiation emitting means and transmitted through the object under examination, the flat panel X-ray detector having numerous radiation detecting elements formed of a semiconductor and arranged longitudinally and transversely on a radiation detecting surface;

signal sampling means for taking radiation detection signals from the radiation detection means at fixed sampling time intervals; and time lag removing means for determining lag-free radiation detection signals by subtracting a radiation detection signal for a lag-behind part from the respective radiation detection signals by a recursive computation, on an assumption that, of said radiation detection signals taken by said signal sampling means at fixed sampling time intervals, the radiation detection signal for a lag-behind part left unread from said radiation detection means within the fixed sampling time intervals, to be read at a next reading time and added to a radiation detection signal actually read at the next reading time, is due to an impulse response formed of one exponential function or a plurality of exponential functions with different attenuation time constants;

wherein said time lac removing means is arranged to perform the recursive computation for removing the lag-behind part from each of the radiation detection signals, based on the following equations A-C:

$$X_k = Y_k - \Sigma_{n=1}^{n} \{\alpha_n \cdot [1-\exp(T_n)] \cdot \exp(T_n) \cdot S_{nk}\} \quad\quad A$$

$$T_n = -\Delta t/\tau_n \quad\quad B$$

$$S_{nk} = X_{k-1} + \exp(T_n) \cdot S_{n(k-1)} \quad\quad C$$

where $\Delta t$: the sampling time interval;

k: a subscript representing a k-th point of time in a sampling time series;

$Y_k$: an X-ray detection signal taken at the k-th sampling time;

$X_k$: a lag-free X-ray detection signal with a lag-behind part removed from the signal $Y_k$;

$X_{k-1}$: a signal $X_k$ taken at a preceding point of time;

$S_{n(k-1)}$: an $S_n$ at a preceding point of time;

exp: an exponential function;

N: the number of exponential function with different time constants forming the impulse response;

n: a subscript representing one of the exponential functions forming the impulse response;

$\alpha_n$: intensity of exponential function n; and $\tau_n$: an attenuation time constant of exponential function n; and wherein said radiographic images being derived from said lag-free radiation detection signals obtained by said time lag removing means.

2. A radiographic apparatus as defined in claim 1, wherein said signal sampling means is arranged to start taking the radiation detection signals at the sampling time intervals before emission of the radiation, and said time lag removing means is arranged to obtain the lag-free radiation detection signals by using said radiation detection signals taken before emission of the radiation.

3. A radiographic apparatus as defined in claim 1, wherein said signal sampling means is arranged to take the radiation detection signals for one radiographic image continually at each period between the sampling time intervals, and said time lag removing means is arranged to obtain, continually at each period between the sampling time intervals, the lag-free radiation detection signals corresponding to the radiation detection signals for the one radiographic image, the radiographic images being obtained continually at the sampling time intervals from said lag-free radiation detection signals for dynamic display.

4. A radiographic apparatus as defined in claim 3, wherein a computation of said lag-free radiation detection signals and an acquisition and dynamic image display of the radiographic images are performed in real time.

* * * * *